United States Patent [19]

Palmieri

[11] 4,415,107
[45] Nov. 15, 1983

[54] APPARATUS FOR INTRAOPERATIVE DIAGNOSIS

[76] Inventor: Beniamino Palmieri, Boito Street No. 45, Modena, Italy

[21] Appl. No.: 236,574

[22] Filed: Feb. 20, 1981

[30] Foreign Application Priority Data

Jun. 23, 1980 [IT] Italy .............................. 22959 A/80

[51] Int. Cl.³ .............................................. B26F 3/00
[52] U.S. Cl. ...................................... 225/93.5; 225/1; 241/DIG. 37; 356/36
[58] Field of Search ......................... 225/93.5, 1, 2, 96; 241/DIG. 37, 1, 23, 65; 356/36, 38

[56] References Cited

U.S. PATENT DOCUMENTS

| | | | |
|---|---|---|---|
| 3,116,863 | 1/1964 | Long .............................. | 225/93.5 X |
| 3,797,757 | 3/1974 | Marshall ........................ | 225/93.5 X |
| 4,023,734 | 5/1977 | Hervé et al. ........... | 241/DIG. 37 X |
| 4,255,216 | 3/1981 | Conant et al. ................. | 225/93.5 X |

FOREIGN PATENT DOCUMENTS 3003383 8/1981 Fed. Rep. of Germany ..... 225/93.5

*Primary Examiner*—Frank T. Yost
*Attorney, Agent, or Firm*—Bucknam and Archer

[57] ABSTRACT

An apparatus for intraoperative diagnosis is described which comprises a refrigerating device adapted to sprinkle a cryogenic liquid on the surface of a slide whereby the surface of the slide is cooled to at least −4° C. up to −8° C., at least one cooling fan which increases the evaporation of the cryogenic liquid and permits to achieve the necessary hypothemia on the slide; an automatic appositor which permits to exert a measurable and graduated pressure onto the section of the organ which has been interposed between the appositor and the slide at the time in which the section has reached a predetermined temperature. The appositor is provided with means for varying automatically the pressure during the advance of the slide. The refrigerating device comprises a cylinder containing a cryogenic liquid. The invention also resides in the method of carrying out histological analysis which consists of placing a section of tissue under examination on a slide, cooling vigorously the slide whereby the tissue undergoes a thermic shock and exfoliates on the slide. Pressure is applied after the section of tissue has been cooled.

8 Claims, 1 Drawing Figure

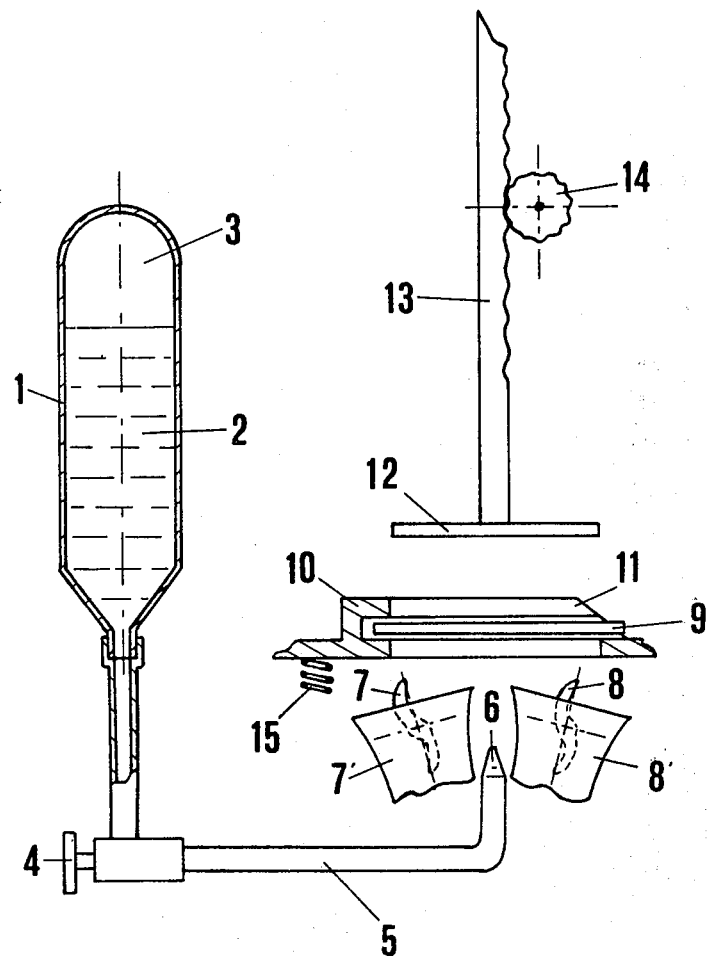

APPARATUS FOR INTRAOPERATIVE DIAGNOSIS

The present invention relates to apparatuses for intraoperative diagnosis by means of "freeze imprinting". This apparatus will be defined hereinbelow for short as a "cryoappositor".

At present, intraoperative diagnosis is based on the use of the freezing cryotome. In actual practice, the surgeon takes a section of the tissue from the diseased part of the patient and gives this section to the pathologist who first freezes the section of the tissue and then cuts it in sections, applies color and carries out in this manner the microscopic diagnosis.

A complementary method, although inaccurate, consists of different technique, namely simply apposition of the operative section. In this manner in general, very small amounts of cellular material is obtained, frequently in poor condition because of the mechanical stresses due to sliding to which the cellular material has been subjected.

The cryoappositor according to the present invention permits to achieve very substantial advantages with respect to the two previously known methods because essentially, it permits to achieve a histological analysis in a monolayer. In fact, the apparatus according to the present invention is based on an original concept according to which the microscopic reproduction of a normal or a pathological organ is so much more trustworthy and accurate, the thinner is the layer of cells being examined under the microscope. Indeed the ideal conditions would be to examine a monocellular layer which reproduces the structure exactly. In this manner one will see in the positive picture the cells of the parenchyma, that is, the epithelial and other tissues which perform the special functions of the organ and in the negative picture vessels and connective tissue, and stroma which will form some pockets. The pockets may be interpreted also quantitatively.

The concept is realized according to the present invention by creating a thermic shock between the section of the organ and the slide which is used as support in such a manner that as a result of the temperature gradient the cells are induced to exfoliate to form a monolayer on the slide, while keeping intact the submicroscopic arrangement, and particularly the enzimatic liposomial arrangement. In order to illustrate the method according to the present invention, it is proper to refer to the sensation of cold which one receives when he touches with naked hands a frozen surface. It is well known that one receives a sensation of instantaneous adhesiveness between the two systems at different temperature. In reality if the cold surface is at a sufficiently low temperature, the hands leave on the surface a thin cellular layer.

The cryoappositor according to the present invention consists essentially of the following: (1) a freezing device which permits to sprinkle a cryogenic liquid on the surface of a slide so as to lower the temperature of the surface to at least about $-4°$ C. and up to about $-8°$ C.; (2) at least one fan for cooling to favor the evaporation of the cryogenic liquid and to contribute to create on the slide the necessary hypothermia and (3) an automatic appositor which may be adjusted with a thermostat to a predetermined temperature and which permits to exert a pressure in predetermined and measurable amounts depending on the organ being examined on the section of the organ which is interposed between the appositor and the slide at the time when this section has reached the ideal temperature. Optionally, the apparatus also comprises a device for automatically advancing the slide which permits to achieve several appositions on the same slide at different pressure.

FIG. 1 illustrates schematically the cryoappositor according to the present invention.

By reference to FIG. 1, numeral 1 is a cylinder of cryogenic liquid, for instance ethyl chloride which is designated by numeral 2.

Numeral 3 is a gas slightly pressurized above the level of the cryogenic liquid. Numeral 4 is a faucet which permits the liquid 2 to reach by means of the circuit 5 nozzle 6 so that it is possible to sprinkle the same liquid on a limited and focalized portion of the slide 9. Numerals 7 and 8 represent fans which direct a jet of air suitably delimited by deflectors 7' and 8' on the lower surface of the slide so that the evaporation of the cryogenic liquid is accelerated. In this manner the cooling of the slide is rendered more rapid. The latter is controlled by suitable guides 10 and 11 which permit the lateral sliding. The anatomic section to be exfoliated is placed on the slide 9 and is compressed on it by means of appositor 12. The latter by means of a toothed shaft 13 and a toothed wheel 14 in a pinion-gear arrangement exerts a graduated pressure on the section being analyzed. The anatomic section is placed onto the slide 9 after the latter has reached a stationary temperature. This usually occurs 3-4 minutes after the faucet 4 has been opened and after simultaneously the cooling fan or fans have been put in operation.

Eventually the guides 10 and 11 and consequently, also the slide 9 are subjected to vibration by means of a motor, schematically represented in the figure by numeral 15 which permits to subject the anatomic section to a mechanical shock which overlaps with the thermic shock and facilitates the exfoliation.

Finally, the apparatus may be provided with a device for automatically advancing the slide 9 so that several appositions at different pressures may be made on the same slide and information may be obtained with respect to the degree of separation of the cells after the second, third, fourth, etc. apposition. In this manner, it is possible to reconstruct, layer by layer, the properties of the tissue which would result indistinguishable by means of a conventional histological examination. The degree of cellular adhesion to the cooled slide may be assumed also to be an indication of the density of the neoplasiae.

It is clear from the foregoing that the apparatus illustrated in the figure and described hereinabove may be modified within the scope of the present invention. For instance, the fans 7 and 8 and vibrating device 15 may be electrically activated by a battery or by electric current. The cryogenic liquid may consist in the case in which it is desirable to achieve particular effects, of gaseous material which can remain in the liquid state at very low temperatures, such as liquid nitrogen. The pressurized gas 3 may consist of the same vapors of the cryogenic liquid and the exit of the same liquid at the time the faucet is opened may be accelerated, for instance, by means of a sleeve which has a warming effect and which is applied around the cylinder. A characteristic of the cryoappositor according to the present invention which may not be overlooked consists of its small dimensions, at the most in the range of 30-40 cm., a feature which makes it extremely easy to handle and very easy to transport.

The cooling period varies from one bioptic section to another and also depends upon the thickness of the slide, but in any event, the period of time is very short, being always in the range of a few tenths of a second. At the end of a cooling period, the section is removed with tweezers, the slide is removed from the guide and the slide is then ready for instantaneous application of color.

According to another embodiment, the slide may be precolored, in which case the system requires not more than 3–5 minutes total from the time when the apparatus begins to be in operation up to the time when the slide is ready for the diagnostic analysis.

The experiments which have been carried out with the apparatus according to the present invention permit to conclude that in a very short time one can achieve information with respect to:

(1) structure of the parenchima being examined which undergoes exfoliation in the form of monolayer on the slide.
(2) properties of the parenchima with respect to the density of the cells which have undergone desquamation.
(3) the presence in the negative of vascular structures.
(4) density of the cells in successive appositions as an index of the excess of cellular layers with respect to the possibility of the stroma being bound.

In addition, the cryoappositor device according to the present invention permits to achieve a very substantial detailed diagnostic study of the cells with respect to the nucleus, nucleoli, mitosis, the presence of mast cells and their quantitization; ratio between cells and cells; in case of tumors, the relationship between neoplastic cells and normal cells; relationship between tissues which are immuno-reactive and normal tissues or pathological tissues as in the case of infiltration in the liver of inflammatory substances or phlogistic reactions in areas of tumors where detailed examination is desirable.

What is claimed is:

1. An apparatus for preparing a section of an organ for intraoperative diagnosis which comprises a refrigerating device which sprinkles a cryogenic liquid on the surface of a slide whereby the surface of the slide is cooled to at least $-4°$ C. up to $-8°$ C., at least one cooling fan which increases the evaporation of the cryogenic liquid to achieve the necessary hypothermia on the slide; an appositor which exerts a measurable and graduated pressure onto the section of the organ which has been interposed between said appositor and the slide at the time in which said section has reached a predetermined temperature.

2. The apparatus according to claim 1 wherein the refrigerating device comprises a cylinder containing a cryogenic liquid.

3. The apparatus according to claim 2 which comprises means for increasing the rate of exit of the liquid from the cylinder.

4. The apparatus according to claim 3 wherein said means are a pressurized gas above the liquid in said cylinder.

5. The apparatus according to claim 1 wherein the refrigerating device comprises a nozzle capable of sprinkling the cryogenic liquid and capable of being oriented onto the central portion of the slide.

6. The apparatus according to claim 1 wherein the cryogenic liquid is ethyl chloride or other liquid having a low boiling point.

7. The apparatus according to claim 1 wherein the cryogenic liquid consists of a liquefied gas.

8. The apparatus according to claim 5 wherein the liquefied gas is nitrogen.

* * * * *